(12) United States Patent
Furlan

(10) Patent No.: US 10,767,218 B2
(45) Date of Patent: Sep. 8, 2020

(54) METHOD FOR REDUCING QUANTIFICATION ERRORS CAUSED BY REACTION VOLUME DEVIATIONS IN DIGITAL POLYMERASE CHAIN REACTION

(71) Applicant: Roche Molecular Systems, Inc., Pleasanton, CA (US)

(72) Inventor: Alan Furlan, Zug (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 101 days.

(21) Appl. No.: 15/712,977

(22) Filed: Sep. 22, 2017

(65) Prior Publication Data
US 2018/0087090 A1    Mar. 29, 2018

(30) Foreign Application Priority Data
Sep. 23, 2016   (EP) .................................... 16002057

(51) Int. Cl.
| C12P 19/34 | (2006.01) |
| C12Q 1/686 | (2018.01) |
| C12Q 1/6851 | (2018.01) |
| C12Q 1/6837 | (2018.01) |
| C12Q 1/70 | (2006.01) |
| G01N 33/483 | (2006.01) |

(52) U.S. Cl.
CPC .......... C12Q 1/686 (2013.01); C12Q 1/6837 (2013.01); C12Q 1/6851 (2013.01); *C12Q 1/701* (2013.01); *G01N 33/4833* (2013.01)

(58) Field of Classification Search
None
See application file for complete search history.

(56) References Cited

U.S. PATENT DOCUMENTS

| 9,898,820 B2 | 2/2018 | Chu et al. |
| 10,403,000 B2 | 9/2019 | Chu et al. |
| 2007/0161114 A1* | 7/2007 | Curtis ..................... G01F 22/00 436/164 |
| 2010/0255459 A1* | 10/2010 | Bosch Navarro ...... C12Q 1/701 435/5 |
| 2013/0302792 A1 | 11/2013 | Hindson et al. |
| 2018/0230515 A1* | 8/2018 | Betschart ............. C12Q 1/6851 |

FOREIGN PATENT DOCUMENTS

WO    WO03050515    6/2003

OTHER PUBLICATIONS

Dong et al., Scientific Reports 2015, 5:13174, DOI: 10.1038/srep13174 "Comparison of four digital PCR platforms for accurate quantification of DNA copy number of a certified plasmid DNA reference material".
Dong et al., Anal Bioanal Chem (2014) 406:1701-1712 DOI 10.1007/s00216-013-7546-1 "Evaluation of droplet digital PCR for characterizing plasmid reference material used for quantifying ammonia oxidizers and denitrifiers".
McGown et al., Analytical Biochemistry, vol. 258, No. 1, Apr. 1, 1998 (Apr. 1, 1998), pp. 155-157, XP055340416,Amsterdam, NL C12Q ISSN: 0003-2697, DOI:10.1006/abio.1998.2621 abstract; Fig 2.
EP16002057.4 search report, (2017).

* cited by examiner

*Primary Examiner* — Kenneth R Horlick
(74) *Attorney, Agent, or Firm* — Maneesh Gupta; Pamela C. Ancona

(57) ABSTRACT

The present disclosure relates to a method for reducing quantification errors caused by reaction volume deviations in digital polymerase chain reaction (dPCR) and to a method for determining the amount or concentration of a nucleic acid of interest in a sample with dPCR.

20 Claims, 1 Drawing Sheet

METHOD FOR REDUCING QUANTIFICATION ERRORS CAUSED BY REACTION VOLUME DEVIATIONS IN DIGITAL POLYMERASE CHAIN REACTION

CROSS-REFERENCE TO RELATED APPLICATIONS

The present application claims the benefit of priority under 35 U.S.C. § 119(a) of EP16002057.4, filed Sep. 23, 2016. Reference is also made to EP16183569.9, filed Aug. 10, 2016; EP16002058.2, filed Sep. 23, 2016; and EP16191425.4, filed Sep. 29, 2016; and EP16400045.7, EP16191771.1, EP16400044.0; EP16191811.5, each filed September 30. The disclosures of each of these applications to are incorporated herein by reference in their entireties.

FIELD OF THE DISCLOSURE

The present disclosure relates to a method for reducing quantification errors caused by reaction volume deviations in digital polymerase chain reaction (dPCR) and to a method for determining the amount or concentration of a nucleic acid of interest in a sample with dPCR.

BACKGROUND

For many biological, biochemical, diagnostic or therapeutic purposes, it is necessary to accurately and precisely determine the amount or concentration of a nucleic acid in a sample. dPCR is a rather new approach to nucleic acid detection and quantification that offers an alternative method to conventional real-time quantitative PCR for absolute quantification of nucleic acids and rare allele detection. dPCR works by partitioning a sample of nucleic acids into many individual, parallel PCR reactions; some of these reactions contain the target molecule (positive) while others do not (negative). Following PCR analysis, the fraction of negative reactions is used to generate an absolute count of the number of target molecules in the sample. One of the key advantages of dPCR over real-time PCR is its superior accuracy of quantification. This advantage relies on inherent properties of dPCR as quantification only requires correct counting of positive partitions and the knowledge of the theoretical partition volume (the count number is not very sensitive to PCR efficiency). A quantification standard is not required. This eliminates potential quantification errors caused by the standard itself.

The prior art provides methods in order to identify incorrect positive or negative counts and for calibrating or normalizing signals in droplet-based assay (US 2013/0302792 A1). This normalization should improve the separation between positive and negative counts. Hence the normalization reduces the risk of false positive or negative counts. The ultimate goal is to improve the accuracy and precision of the determination of the nucleic acid concentration by correcting the signal obtained for the nucleic acid.

However, the methods of the prior art do not account for quantification errors in PCR due to situations, in which the true volume in the dPCR reaction areas differs from the expected or intended one.

Accordingly, there is a need for methods of quantifying a nucleic acid of interest by dPCR, which reduce quantification errors caused by reaction volume deviations. The object of the present disclosure was to provide those methods.

SUMMARY

The object was solved by methods based on digital polymerase chain reaction (dPCR) in which the volume in each reaction area is quantified and included into the calculation of the amount or concentration of the nucleic acid of interest. This may be done by adding a fill control marker to each reaction area.

Accordingly, the present disclosure provides not only a highly accurate and precise method to quantify a nucleic acid by dPCR, but also the volume used in dPCR, which allows for more precise and accurate determination of the amount or concentration of a nucleic acid of interest in a sample. Particularly, the above methods allow for correction of quantification errors e.g. due to non-uniform reaction area sizes or deviations of the average reaction area volume. Moreover, quantification errors caused by invalid (e.g. empty or almost empty) reaction areas may be eliminated.

Thus, the disclosure provides a method for reducing quantification errors caused by reaction volume deviations in digital polymerase chain reaction (dPCR), wherein the amount or concentration of a nucleic acid of interest is quantified in an array of reaction areas, the method comprising a) adding a fill control marker to each reaction area of the array of reaction areas used in dPCR; b) quantifying the reaction volume in each reaction area; and c) calculating the amount or concentration of the nucleic acid of interest as number of nucleic acid as determined by dPCR in a or per volume, wherein the volume is the sum of the reaction volumes as determined in step b).

Also provided is a method for determining the amount or concentration of a nucleic acid of interest in a sample, the method comprising the steps of:

a) providing a sample suspected of containing the nucleic acid of interest;
b) performing a dPCR with the sample in each reaction area of an array of reaction areas;
c) quantifying the reaction volume in each reaction area; and
d) calculating the amount or concentration of the nucleic acid of interest as number of nucleic acid as determined in step b) in a or per volume, wherein the volume is the sum of the reaction volumes as determined in step c).

Figure 1:
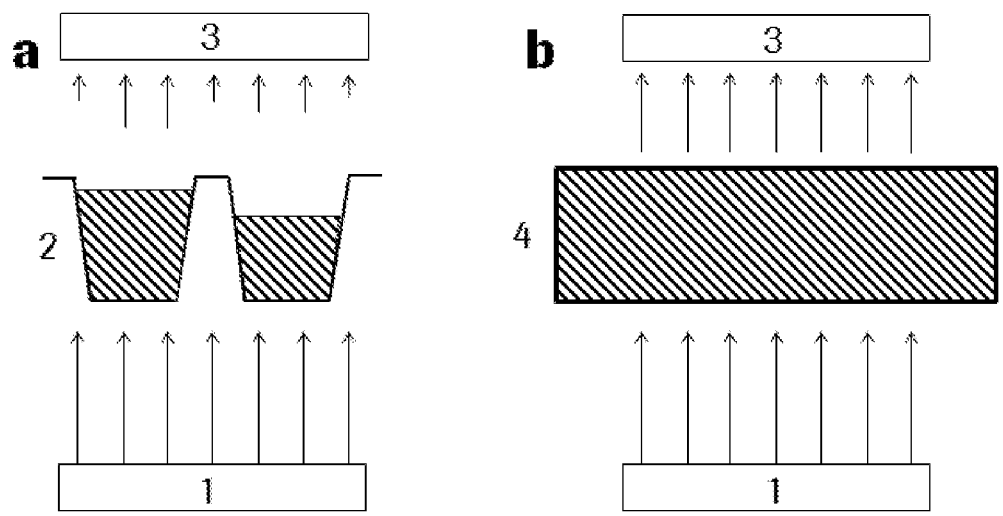
FIG. 1 illustrates an exemplary setup for evaluating the height of a filled reaction area in a dPCR assay (a) Light source (1) illuminates a dPCR array filled with a control marker (2). The fluorescence signal of the control marker originating from the individual reaction areas, which reaches detector (3), is essentially proportional to the height of the liquid in each reaction area. (b) For calibration, the height is determined using a calibration cuvette with a well-known height (4) filled with the same control marker solution. The signals are recorded under the same conditions as in experiment (a).

a) Valid positive reaction area
b) Valid positive reaction area (fill level above threshold)
c) Valid negative reaction area
d) Valid negative reaction area (fill level above threshold)
e) Invalid reaction area (no reaction mix present)
f) Invalid reaction area (fill level below threshold).

DETAILED DESCRIPTION

In a first aspect, the present disclosure relates to a method for reducing quantification errors caused by reaction volume deviations in digital polymerase chain reaction (dPCR), wherein the amount or concentration of a nucleic acid of interest is quantified in an array of reaction areas, the method comprising
a) adding a fill control marker to each reaction area of the array of reaction areas used in dPCR;
b) quantifying the reaction volume in each reaction area; and
c) calculating the amount or concentration of the nucleic acid of interest as number of nucleic acid as determined by dPCR in a or per volume, wherein the volume is the sum of the reaction volumes as determined in step b).

As detailed above, a method to reliably determine the amount or concentration of a nucleic acid is of particular relevance in several industrial applications, e.g. in the medical field. For several aspects it may not only be necessary to clarify whether or not a nucleic acid is present in the sample, but it may be required to determine—as precisely and accurately as possible—the amount or concentration of the nucleic acid in the sample, e.g. a sample obtained from a patient or product. This might be of interest e.g. in the diagnosis of the severity of a disease or in environmental technology or quality control of products, e.g. in order to define contaminations or impurities.

Present dPCR methods focus on the determination of the number of nucleic acid present in the intended volume. However in order to determine the amount of the nucleic acid in question in a specific volume or their concentration per volume, it is also required to know the actual and correct volume. With the dPCR methods of the present disclosure, the number of nucleic acids (i.e. the copies of a nucleic acid if interest) as well as the volume, in which they are contained, are determined simultaneously, thus providing a more accurate result.

dPCR (digital polymerase chain reaction, digital PCR or DigitalPCR) is a biotechnology refinement of conventional polymerase chain reaction methods that can be used to directly quantify and optionally clonally amplify nucleic acids including DNA, cDNA, RNA or mixtures thereof. The key difference between dPCR and traditional PCR (e.g. qPCR) lies in the method of measuring nucleic acids amount, with the former being a more precise and accurate method than PCR, though also more prone to error in the hands of inexperienced users. The smaller dynamic range of dPCR may require dilutions of the sample. dPCR also carries out a single reaction within a sample, however the sample is separated into a large number of partitions or reaction areas and the reaction is carried out in each partition or reaction area individually. This separation allows a more reliable collection and sensitive measurement of nucleic acid amounts. Moreover, the method allows for accurate quantification.

As detailed above, the dPCR sample is partitioned so that individual nucleic acid molecules within the sample are localized and concentrated within many separate regions (reaction areas). The partitioning of the sample allows to estimate the number of nucleic acids by assuming that the molecule population follows the Poisson distribution. As a result, each part will contain a negative or positive reaction ("0" or "1", respectively). After PCR amplification, nucleic acids may be quantified by counting the regions that contain PCR end-product positive reactions. In conventional quantitative PCR, the quantitation result may depend on the amplification efficiency of the PCR process. dPCR, however, is not dependent on the number of amplification cycles to determine the initial sample amount, eliminating the reliance on uncertain exponential data to quantify target nucleic acids and therefore provides absolute quantification.

The first aspect of the present disclosure relates to a method for reducing quantification errors caused by reaction volume deviations.

Reaction volume deviations may result in non-uniform volumes in the reaction areas. The width of the size distribution of the areas affects the count rate and hence the accuracy of the calculated nucleic acid concentration. This quantification error is negligible at low copy numbers per area, but may become large at high copy numbers per area. This effect can be illustrated by a thought experiment whereby one area becomes very large while all others shrink towards zero. In this case the positive count would obviously tend towards one, resulting in an extreme under-quantification.

Alternatively or additionally, the reaction volume deviations may be due to the fact that the average reaction area volume differs from the intended or expected one, e.g. as predetermined by a calibration value.

Both in droplet-based and array-based dPCR systems, uncertainties in the average partition volume were found to be a major source of accuracy errors in current systems (Dong et al., 2015, Sci. Rep. 5, 13174 and Dong et al., 2014, Anal. Bioanal. Chem. 406, 1701-1712).

Average reaction area volumes may change due to changes in reaction mix composition (in the case of dPCR arrays detergents have an effect on the meniscus forming at the interface of the reaction mix and the sealing fluid), changes in reaction area depths caused by the production process of the arrays (e.g. changes of the molding tools used for producing the arrays may be associated with geometric changes of the reaction areas) or changes in filling degree of the reaction area due to the filling speed.

In the first step of the method of the first aspect, a fill control marker is added to each reaction area of an array of reaction areas used in dPCR in order to reduce quantification errors caused by reaction volume deviations. The fill control marker may be any substance or composition allowing quantifying the reaction volume in each reaction area.

Accordingly, the fill control marker may consist of or comprise any detectable label. The term "label" as used herein generally refers to any kind of substance or agent which can be used to visualize, detect, analyze and/or quantify the volume in a reaction area. A label may, for example, be a dye that renders the volume optically detectable and/or optically distinguishable. The label indicates the volume of each reaction area, e.g., in a flow stream, in a multiwall-plate, on a chip, in an array or field of view, among others. The marker may have any suitable uniform or nonuniform distribution in each reaction area. For example, the marker may be distributed substantially uniformly throughout a reaction area, may be localized to a perimeter of the reaction area (e.g., localized to a skin that encapsulates the droplet or a surface that covers the reaction area, e.g. in a well), or may have one or more discrete localizations within the reaction area (e.g., if the marker is a particle (such as a bead or quantum dot, among others)).

A label according to the present disclosure may include, but is not limited to, radioisotopes such as, e.g., $^{35}$Sulphur ($^{35}$S), $^{32}$Phosphorus ($^{32}$P), $^{33}$Phosphorus ($^{33}$P), $^{3}$H or $^{14}$C, any colored (e.g. 2,4-dinitrophenol) or luminescent, specifically fluorescent, molecule or an absorbance marker (non-fluorescing or fluorescent) which can be detected and/or visualized by means of luminescence analysis such as fluorescein dyes including, but not limited to, carboxyfluorescein (FAM), 6-carboxy-4',5'-dichloro-2'7'-dimethoxyfluorescein (JOE), fluoresceinisothiocyanat (FITC), tetrachlorofluorescein (TET), and hexachlorofluorescein, rhodamine dyes such as, e.g., carboxy-X-rhodamine (ROX), Texas Red and tetramethylrhodamine (TAMRA), cyanine dyes such as pyrylium cyanine dyes, DY548, Quasar 570, or Cy3, Cy5, Alexa 568, and alike. Fluorescent labels are commercially available from diverse suppliers including, for example, Invitrogen™ (USA).

The choice of the label is typically determined by its physical properties (e.g. spectral properties), by the availability of equipment for detecting and by the label(s) used in the detection of the nucleic acids in the dPCR. Labels as well as their detection strategies are well known to the person skilled in the art.

For example, the signal may be a fluorescence signal. If two or more different fluorescence signals are measured from each reaction area (one for PCR and one as fill control marker), the signals may, for example, be detected at distinct wavelengths or wavebands. Alternatively, the fluorescence signals may be measured at the same wavelength/waveband after excitation with different wavelengths or wavebands of light (e.g., excitation at different times or at different positions), among others. Two or more fluorescence signals may be detected via respective distinct fluorophores.

In some embodiments, the fill control marker may be not coupled to an amplification reaction and thus serves as a passive reference. In some embodiments, the fill control marker may be additionally used as a control signal detected from a control amplification reaction. The control amplification reaction may measure amplification of an exogenous or endogenous template. Specifically, the label is stable during the method, not subject to bleaching, independent from the amplification reaction and/or temperature invariant.

In a second step of the method of the first aspect, the reaction volume in each reaction area is quantified. The reaction volume is quantified based on the signal provided by the fill control marker. The volume of the reaction area may be determined based on the amount or concentration of fill control marker detected in each reaction area. Methods for determining the amount or concentration of a marker will depend from the marker used and are well known in the art. For example, radioactivity may be measured, if radioisotopes are used. Specifically, a fluorescence marker is used, which can be detected and/or quantified by means of fluorescence.

In addition to the determination of the volume, the fill control marker may be used as normalizing factor for the signal obtained for the dPCR and/or to eliminate invalid samples form the determination (see also below).

As a third step, the amount or concentration of the nucleic acid of interest is calculated as number of nucleic acid as determined by dPCR in a or per volume, wherein the volume is the sum of the reaction volumes as determined in the second step. Further details are given below.

In a second aspect, the present disclosure relates to a method for determining the amount or concentration of a nucleic acid of interest in a sample, the method comprising the steps of:
a) providing a sample suspected of containing the nucleic acid of interest;
b) performing a dPCR with the sample in each reaction area of an array of reaction areas;
c) quantifying the reaction volume in each reaction area; and
d) calculating the amount or concentration of the nucleic acid of interest as number of nucleic acid as determined in step b) in a or per volume, wherein the volume is the sum of the reaction volumes as determined in step c).

In a first step of the method of the disclosure, a sample suspected of containing the nucleic acid of interest is provided.

The sample may be any sample suspected of containing the nucleic acid in question, including a sample from a subject. A sample is a limited quantity of material which is intended to be identical to and represent a larger amount of that material(s). An act of obtaining a sample can be done by a person or automatically. Samples can be taken or provided for testing, analysis, inspection, investigation, demonstration, or trial use. Sometimes, sampling may be continuously ongoing. The sample may comprise or consist of a solid, a liquid or a gas; it may be material of some intermediate characteristics such as gel or sputum, tissue, organisms, or a combination of these. Specifically, the sample is liquid or a suspension which allows for easy distribution.

Even if a material sample is not countable as individual items, the quantity of the sample may still be describable in terms of its volume, mass, size, or other such dimensions. A solid sample can come in one or a few discrete pieces, or can be fragmented, granular, or powdered.

The sample in the present context is a quantity of material that is suspected of containing one or more nucleic acids that are to be detected or measured and quantified. As used herein, the term includes—without limitation—a specimen (e.g., a biopsy or medical specimen), a culture (e.g., microbiological culture) or an environmental sample such as water or soil. Samples may be from a subject, such as an animal or human, they may be fluid, solid (e.g., stool), a suspension or tissue. The term "sample from a subject" includes all biological fluids, excretions and tissues isolated from any given subject. Specifically, the subject is an animal, more specifically a mammal or still more specifically a human. The sample may be obtained from all of the various families of domestic animals, as well as feral or wild animals, including, but not limited to, such animals as ungulates, bear, fish, rodents, etc.

Examples of samples include, but are not limited to, cell or tissue cultures, blood, blood serum, blood plasma, needle aspirate, urine, semen, seminal fluid, seminal plasma, prostatic fluid, excreta, tears, saliva, sweat, biopsy, ascites, cerebrospinal fluid, pleural fluid, amniotic fluid, peritoneal fluid, interstitial fluid, sputum, milk, lymph, bronchial and other lavage samples, or tissue extract samples The source of the sample may be solid tissue as from a fresh, frozen and/or preserved organ or tissue sample or biopsy or aspirate; or cells from any time in gestation or development of the subject.

The sample may contain compounds which are not naturally intermixed with the source of the sample in nature such as preservatives, anticoagulants, buffers, fixatives, nutrients, antibiotics, or the like.

If the sample is not ready or suitable for dPCR, further processing before being used in dPCR might be required. Usually, the samples need to be processed for dPCR by e.g. diluting the sample (to obtain a concentration of nucleic acids allowing for dPCR), removing disturbing components, adding reagents required for dPCR etc. The processing may comprise a multitude of different steps and techniques, which will depend on various aspects, including the nature of the sample, the type of nucleic acid of interest and the dPCR method used. Typically, the processing includes purification steps and/or dilution or concentration steps. Methods for purifying nucleic acids are well-known in the art and include—without limitation—homogenization, washing, centrifugation, extraction, etc. It might be necessary to preserve the sample, e.g. by disruption of the sample, by adding preservatives, by freezing or drying the sample. For disruption of the sample obtained, physical force (e.g. a polytron, grinding or freezing) or chemical methods (e.g. lysis of cells) may be used. A detergent or a chaotrope may be used for homogenization. Nucleic acids may be extracted by the use of acid phenol/chloroform, filters, glass particles or chromatography (e.g. with appropriate nucleic acids as binding partner). It might be necessary to store the sample at any time of the processing (at the beginning, during and/or at the end of the processing). For this it might be necessary or suitable to add an appropriate medium, such as a buffered saline. It might be required to remove contaminants and/or nucleic acids, which are not of interest or might be disturbing. Enzymes may be used for removal of contaminants (such as a DNase, an RNase and/or a proteinase) or protection of the nucleic acid of interest (such as a DNase inhibitor or an RNase inhibitor). For inactivation of enzymes a heating step might be appropriate. Removal agents may be used in order to remove undesired components such as divalent cations ($Ca^{2+}$ and $Mg^{2+}$). Washing steps might be required to exchange media.

As detailed above, for dPCR the nucleic acid of interest has to be present in an appropriate amount or concentration during the dPCR. Accordingly, appropriate dilution or concentration steps might be required. Dilution of nucleic acid is usually performed by adding a solvent (such as an appropriate medium for the steps to follow, e.g. a dPCR medium or dPCR buffer). It may be accompanied by washing steps, if e.g. removal of undesired components or concentration in order to obtain certain final concentrations should be intended or required. Concentration may be done by any enrichment procedure such as immunocapture, centrifugation, alcohol precipitation and the use of a binding matrix. After the processing, the sample is ready for dPCR, which is to follow in step b) of the method of the disclosure according to the second aspect.

As detailed above, the sample contains a nucleic acid of interest, the amount or concentration of which is to be determined in the method of the present disclosure. A nucleic acid is a biopolymer essential for all known forms of life. Therefore, nucleic acids may be used as indicator for a particular organism, but also e.g. in case of mutations or naturally occurring variants, as indicator for a disease. Nucleic acids, which include DNA (deoxyribonucleic acid) and RNA (ribonucleic acid), are made from monomers known as nucleotides. Each nucleotide has three components: a 5-carbon sugar, a phosphate group, and a nitrogenous base. If the sugar is deoxyribose, the polymer is DNA. If the sugar is ribose, the polymer is RNA. Nucleic acids are among the most important biological macromolecules. They are found in abundance in all living organisms, where they function in encoding, transmitting and expressing genetic information—in other words, information is conveyed through the nucleic acid sequence, or the order of nucleotides within a DNA or RNA molecule. Experimental studies of nucleic acids constitute a major part of modern biological and medical research, and form a foundation for genome and forensic science, as well as the biotechnology and pharmaceutical industries. Accordingly, the method of the disclosure may be used in any of these fields.

The nucleic acid may be indicative of a microorganism (such as a pathogen) and may be useful in the diagnosis of a disease, such as an infection. Infections may be caused by bacteria, viruses, fungi, and parasites or other nucleic acid containing objects. The pathogen may be exogenous (acquired from environmental or animal sources or from other persons) or endogenous (from the normal flora). Samples may be selected on the basis of signs and symptoms, should be representative of the disease process, and should be collected before administration of antimicrobial agents. The amount of the nucleic acid in the unprocessed sample may be indicative of the severity of the disease.

Alternatively, the nucleic acid may be indicative of a genetic disorder. A genetic disorder is a genetic problem caused by one or more abnormalities in the genome, especially a condition that is present from birth (congenital). Most genetic disorders are quite rare and affect one person in every several thousands or millions. Genetic disorders may or may not be heritable, i.e., passed down from the parents' genes. In non-heritable genetic disorders, defects may be caused by new mutations or changes to the DNA. In such cases, the defect will only be heritable if it occurs in the germ line. The same disease, such as some forms of cancer, may be caused by an inherited genetic condition in some people, by new mutations in other people, and mainly by environmental causes in still other people. Evidently, the amount of nucleic acid with mutation may be indicative of the disease state.

In the methods of the present disclosure, the amount or concentration of nucleic acids is determined. The amount of substance is a standards-defined quantity. The International System of Units (SI) defines the amount of substance to be proportional to the number of elementary entities present, with the inverse of the Avogadro constant as the proportionality constant (in units of mol). The SI unit for amount of substance is the mole. The mole is defined as the amount of substance that contains an equal number of elementary entities as there are atoms in 12 g of the isotope carbon-12. Therefore, the amount of substance of a sample is calculated as the sample mass divided by the molar mass of the substance. In the present context, the "amount" usually refers to the number of copies of the nucleic acid sequence of interest.

The concentration of a substance is the abundancy of a constituent divided by the total volume of a mixture. Several types of mathematical description can be distinguished: mass concentration, molar concentration, number concentration, and volume concentration. The term concentration can be applied to any kind of chemical mixture, but most frequently it refers to solutes and solvents in solutions. The molar (amount) concentration has variants such as normal concentration and osmotic concentration. Specifically, the concentration is the amount of a constituent given in numbers divided by the total volume of a mixture. In the context of the present disclosure, the concentration is usually "copies per volume".

Specifically, the sample provided is in a liquid, which eases further method steps.

As a next step, dPCR is performed with the sample in each reaction area of an array of reaction areas. In dPCR, the nucleic acid in question is amplified and detected, where a number of individual molecules are each isolated in a separate reaction area. Each reaction area (well, chamber, bead, emulsion, etc.) will have either a negative result, if no starting molecule is present, or a positive result for amplification and detection, if the targeted starting molecule is present. It is a technique where a limiting dilution of the sample is made across a number of separate PCR reactions such that part of the reactions have no template molecules and give a negative amplification result. In counting the number of positive PCR reactions at the reaction endpoint, the individual template molecules present in the original sample one-by-one are counted. PCR-based techniques have the additional advantage of only counting molecules that can be amplified, e.g., that are relevant to the massively parallel PCR step in the sequencing workflow. In the digital PCR-based methods, one distributes the nucleic acid to be analyzed into a number of different reaction areas (such as well, beads, emulsions, gel spots, chambers in a microfluidic device, etc.). It is important that some reaction areas, but not all, contain at least one molecule. Typically, each reaction area will contain one or zero molecules. In practice, there will be a random distribution of molecules into reaction areas such as wells. In the case where a percentage of reaction areas (e.g., 80%) is positive, a number of areas will contain one or more molecules (e.g., an average of 2.2 molecules per well). Statistical methods may be used to calculate the expected total number of molecules in the sample, based on the number of different reaction areas and the number of positives. This will result in a calculated amount or concentration of nucleic acids in the portion that was applied to the different reaction areas. A number of statistical methods based on sampling and probability can be used to arrive at this concentration. An example of such an analysis is given in Dube et al, arXiv:0809.1460v2 "Computation of Maximal Resolution of Copy Number Variation on a Nanofluidic Device using Digital PCR (2008)," found at arxiv.org, citation arXiv:0809.1460v2 [q-bio.GN], first uploaded on 8 Sep. 2008. The publication provides a series of equations that may be used to estimate the concentration of molecules and statistical confidence interval based on the number of reaction areas used in a digital PCR array and the number of positive results. Another example of this type of calculation may be found in U.S. Patent Application US 2009/0239308 A1.

Usually, a Poisson distribution is used to predict the digital regime where only a single DNA amplicon will occur in a randomly discretized volume reactor to favor only one DNA amplicon of interest per reaction volume. In this way, the PCR amplified signal (e.g., a fluorescence) emitted by each reactor volume is the product of only one amplicon and is isolated from all other discrete reactor volumes. Quantification is then achieved by counting how many digital reactors emit an amplified fluorescent signal corresponding to an intercalating dye or a particular DNA polymerase probe sequence. Since each reactor volume is limited to no more than a single DNA strand in the digital regime, one can correctly assume that 100% of its amplified fluorescence signal comes from only that one DNA strand and corresponding primer and probe set. However, a very low-concentration regime is usually not favorable with respect to imprecision of result.

A number of methodologies for dPCR exist. For example, emulsion PCR has been used to prepare small beads with clonally amplified DNA—in essence, each bead contains one type of amplicon of dPCR. Fluorescent probe-based technologies, which can be performed on the PCR products "in situ" (i.e., in the same wells), are particularly well suited for this application. U.S. Pat. No. 6,440,705, contains a more detailed description of this amplification procedure. These amplifications may be carried out in an emulsion or gel, on a bead or in a multiwell plate.

dPCR also includes microfluidic-based technologies where channels and pumps are used to deliver molecules to a number of reaction areas. Suitable microfluidic devices are known in the art.

The dPCR is carried out essentially as a conventional PCR. The nucleic acids (reference or of interest) in a suitable medium are contacted with primers, probes and a thermostable polymerase (e.g. Taq polymerase) and thermocycled (cycles of repeated heating and cooling of the reaction for separation of strands and enzymatic replication. The medium usually contains deoxynucleotides, a buffer solution and ions (e.g. $Mg^{2+}$). The selectivity of PCR results from the use of primers that are complementary to the region targeted for amplification under specific thermal cycling conditions. The resulting amplification product is detected by use of a suitable probe, which is usually labelled, e.g. fluorescence-labelled. For mRNA-based PCR the RNA sample is first reverse-transcribed to complementary DNA (cDNA) with reverse transcriptase.

Typically, the PCR process consists of a series of temperature changes that are repeated 25 to 50 times. These cycles normally consist of three stages: the first, at around 95° C., allows the separation of the nucleic acid's double chain; the second, at a temperature of around 50 to 60° C., allows the binding of the primers with the DNA template; the third, at between 68 to 72° C., facilitates the polymerization carried out by the DNA polymerase. Due to the small size of the fragments the last step is usually omitted in this type of PCR as the enzyme is able to increase their number during the change between the alignment stage and the denaturing stage. In addition, a signal, e.g. fluorescence, is measured with a temperature of, for example, 80° C., in order to reduce the signal caused by the presence of primer dimers when a non-specific dye is used. The temperatures and the timings used depend on a wide variety of parameters, such as: the enzyme used to synthesize the DNA, the concentration of divalent ions and deoxyribonucleotides (dNTPs) in the reaction and the binding temperature of the primers.

In an embodiment, a dPCR method is provided that enables the unique ability to identify a greater number of fluorescent probe sequences (e.g., TaqMan probe sequences) by using multiple color, temporal, and intensity combinations to encode each unique probe sequence. Furthermore, less expensive non TaqMan-probe real-time PCR amplification indicators such as SYBR- or PicoGreen can be used to achieve multiplexed dPCR based on temporal cues alone, intensity cues alone, or intensity and temporal cues combined, thus distinguishing primer pairs at greater degrees with significant cost reductions. These can also be used to enhance controls and normalize results for greater accuracy if desired. The typical multiplexing limits from typical 5-plex qPCR can be increased to as much as 100-plex dPCR with limited spectral bands using fluorescent reporters.

Prior to, simultaneously with or after the dPCR, the reaction volume in each reaction area is quantified. Quantification of volumes is well known in the art.

Volume pertains to the three-dimensional space that is occupied by an object (i.e. solid, liquid, gas, or plasma). Volumes may be calculated based on the dimensions, e.g. the length, width, and height of the occupied space by an object. They are usually expressed in SI units, e.g. cubic centimeter ($cm^3$), cubic meter ($m^3$), liter (L), milliliter (mL), etc.

Therefore, the volume may be determined, when the dimensions are known. If the dPCR is run on an array e.g. a multiwell plate with cylindrical wells, the volume of a liquid in a well can be calculated as volume=$\pi*r^2*$filling height. The radius may be provided by the supplier of the array or measured. Formulas for arrays with other shapes (e.g. cones or cubes) are known as well.

However, as the liquid volume in a reaction area of a dPCR array mainly changes in height, it may be sufficient to determine the height of the liquid in the reaction area. Various optical methods e.g. involving a spectrometer can be used.

In one exemplary embodiment, a calibration measurement is involved using a calibration cuvette with a well-known height, a control dye (e.g. generating a signal proportional to the number of fluorophores per area in the field plane) and a detection system generating signals proportional to the height of the passive control dye in the light path. The height of the liquid in the reaction area of an array is calculated by comparing the signals with those of the calibration cuvette measured under the same conditions. The method is illustrated in FIG. 1.

Alternatively, the volume may be determined based on the mass, if the density is known. The volume may be determined as mass divided by the density. In another embodiment a fill control marker is used. Details on the fill control marker are given above.

As a next step the amount or concentration of the nucleic acid of interest is calculated as number of nucleic acid as determined in step b) in a or per volume, wherein the volume is the sum of the reaction volumes as determined in step c). As detailed above, in the methods of the state of the art, the amount or concentration of the nucleic acid in question is calculated based on the volume intended or expected in each reaction area. The fill control markers used so for have been used for eliminating invalid reaction areas and for correcting false positive or negative results. In the present methods, the fill control marker is used for the determination of the true volume in each reaction area and thus for the determination of the total and true volume analyzed by dPCR. It is evident that knowing the correct volume is important for determining the correct amount of the nucleic acid in question or its concentration. The total volume is the sum of the volumes in the reaction areas. The amount of nucleic acids in numbers is obtained by dPCR. The concentration of the nucleic acid is usually given as number of nucleic acids/volume, e.g. µl.

Accordingly, the concentration may be calculated by dividing the copy number $N_c$ by the sampled liquid volume. The copy number $N_c$ is obtained from the count of positive reaction areas after applying the Poisson correction. The sampled liquid volume V is equal to the sum of the volumes of all reaction areas which were evaluated in the experiment.

Moreover and in addition to the overall correction of concentration calculation based on distribution of reaction area volumes, the fill control marker can be used for normalization of each reaction area in order to identify valid positives and valid negatives and to exclude invalid reaction areas.

Accordingly, the concentration of the nucleic acid of interest is given by:

$$(\text{valid positives}) \Big/ \left( (\text{valid positives} + \text{valid negatives}) * \left( \sum_{i=1}^{n} \text{valid reaction area volume } i \right) \right)$$

if the distribution of reaction volumes is narrow and the copies per partition are <<1 or more general as $$P * C * ((\text{valid positives})/(\text{valid positives} + \text{valid negatives})) \Big/ \left( \sum_{i=1}^{n} \text{valid reaction area volume } i \right)$$

wherein P is the Poisson correction factor. It depends on the ratio of valid positives and negatives, and accounts for the possibility of reaction areas containing more than one copy of nucleic acid. At low copies-per-reaction-area ratio (valid positives<<valid negatives), P=1 and wherein C is a volume distribution correction factor. It depends on the copies-per-reaction-area ratio and the variation of reaction area volumes relative to the average reaction area volume. At low copies-per-reaction-area ratio and a relative reaction area volume variation<10%, C=1.

Additionally, another correction factor must be added. If the sample has been processed prior to use in dPCR, e.g. diluted, the processing and dilution steps should be included into the calculation in order to obtain the amount or concentration of a nucleic acid of interest in the sample analyzed.

In a particular embodiment of the methods of the disclosure, the reaction volume is quantified by quantifying a fill control marker present in each reaction area, particularly wherein the signal of the fill control marker is proportional to the reaction volume in the reaction area. Details on fill control markers and their quantification are given herein. However, if a fill control marker is used, the signal of which is proportional to the reaction volume in the reaction area, the valid reaction area volume may be calculated as follows:

valid reaction area volume $[i]$=(reference reaction area volume)*(intensity of control dye)*const.

More specifically, a correction factor for each reaction area is calculated based on the signal of the fill control marker measured and the signal of the fill control marker expected and wherein the correction factor accounting for a reaction volume deviation is applied to the respective reaction area. The present disclosure uses the signal of the fill control marker as a measure for the overall volume. However, it may also be used to normalize the results of the dPCR. As detailed in US 2013/0302792 A1, the signals obtained in dPCR may be corrected using the signal of a dye, in order to correctly identify positives and negatives. Also empty reaction areas are recognized as empty (or may be filled with oil) and do therefore not add to the total volume of sample, which would lead to a mistake in the finally found concentration of target DNA. So the volume of valid sample is the sum of each individual well with its individual content volume. The correction further increases accuracy and precision of the quantification with dPCR wherein all reaction areas are classified as valid positive, valid negative or invalid reaction areas:

A valid positive reaction area is properly filled with reaction mix and generates a positive PCR signal after amplification.

A valid negative reaction area is properly filled with reaction mix and generates no PCR signal after amplification.

An invalid reaction area is not (or insufficiently) filled with reaction mix or is eliminated because of other characteristics attributed to artefacts.

Having an accurate measure of the total valid volume provides dPCR methods allowing to perform highly absolute quantification of the nucleic acid of interest.

Moreover, the method also allows to eliminate quantification errors caused by non-uniform reaction area volumes. This may be done as follows:

a) The distribution of reaction area volumes is determined in a calibration experiment. Thereby the signals of the fill control marker from each reaction area, which are proportional to the respective reaction area volume, are evaluated.
b) A correction factor is evaluated which accounts for the quantification error caused by this distribution of reaction area volumes.
c) The correction factor C (which depends on the copies-per-reaction area ratio and the relative variation of reaction area volumes, see above) is applied to each concentration determined with this experimental setup.

This solution relies on the assumption that the distribution of reaction area volume remains constant from experiment to experiment. This is the case if the production process for the arrays and the filling process is very stable.

If this is not the case, a more advanced calculation can be applied:
a) The distribution of reaction area volumes is determined in each experiment.
b) The distribution is fitted to a model curve.
c) The model curve is used to evaluate the correction factor for the concentration measured in this particular experiment.

As the liquid volume in a reaction area of a dPCR array may mainly change in height (due to meniscus effects and well depth variations), it may be sufficient to determine the height of the liquid reaction areas.

The solution consists of a calibration measurement using
A calibration cuvette with a well-known height
A fill control marker (generating a signal proportional to the number of fluorophores per area in the field plane)
A detection system generating signals proportional to the height of the fill control marker.

The height of the liquid reaction areas of a sample array (a) are calculated by comparing the signals with those of the calibration cuvette measured under the same conditions.

Accordingly, in another particular embodiment of the methods of the disclosure, the reaction volume in each reaction area is quantified based on the height of the reaction volume in the reaction area, particularly in a well, specifically by using a fill control marker. Further details relating thereto are provided above.

In another particular embodiment of the methods of the disclosure, a reaction area is identified as invalid, if the quantity of the fill control marker in the reaction area is below a lower threshold or optionally above an upper threshold.

Figure 2:
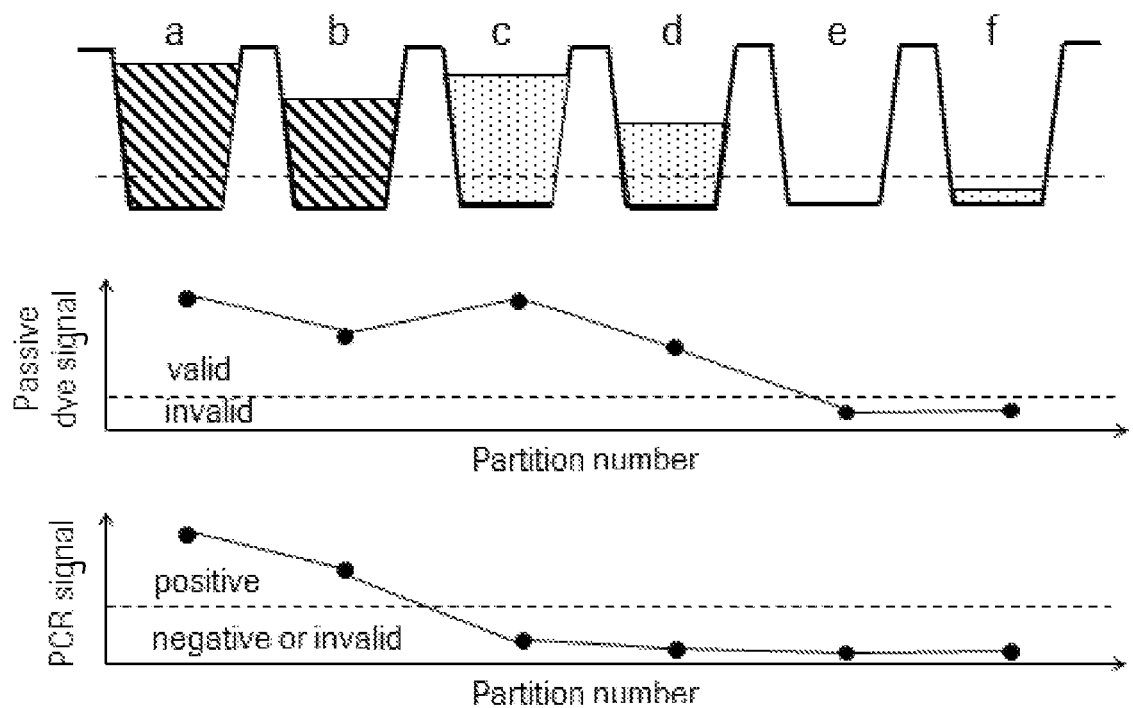
FIG. 2 shows a schematic representation of valid and invalid reaction areas. Invalid reaction areas are discarded from the calculation of the amount or concentration of nucleic acid.

As detailed above, it is important to identify invalid reaction areas. A reaction area may be invalid, because the filling or distribution process prior to dPCR may result in reaction areas of the array with empty or insufficiently filled reaction areas (see wells e) and f) of FIG. 2). If they are misinterpreted as filled wells without nucleic acid (negatives), the sampled volume V is overestimated and the concentration underestimated. These reaction areas can be identified using the fill control marker, e.g. if the signal of the fill control marker is below a lower threshold, and eliminated from the calculation. Alternatively or additionally, if the signal level of the fill control marker from a particular reaction area is above a predefined threshold value, this reaction area may be discarded from the calculation of target concentration. Usually, a reaction area cannot be filled beyond its maximum height. Larger signal levels indicate artefacts that may originate from fluorescing dust particles and other contaminations.

Evidently, the fill control marker can be added to the reaction area at different times, also depending on the assay design, the fill control marker used and its properties. In general, the fill control marker may be added to the reaction areas before or after dPCR is carried out.

For example, the fill control marker can be present in the reaction area before the reagents necessary to carry out the dPCR are added. In one example, the assay marker may be distributed to the array, when the array is produced or manufactured. This option may be chosen, e.g. if the height of the marker is detected, e.g. in a multiwell plate.

Alternatively, the marker may be distributed to the reaction areas along with the dPCR reagents. This is particularly suitable if the amount or concentration of the fill control marker is measured. In the methods of the disclosure, the fill control marker is specifically added to the PCR reaction mix before being distributed to the reaction areas.

In another particular embodiment of the methods of the disclosure, the fill control marker is a fluorescence marker or an absorbance marker.

A wide range of fluorescence markers can be used as fill control markers in accordance with the present disclosure. Each fluorescence marker has a characteristic peak excitation and emission wavelength, and the emission spectra often overlap. Consequently, the combination of fluorescence markers used for dPCR and fill control depends on the wavelength of the lamp(s) or laser(s) used to excite the fluorochromes, the detectors available and the properties of the markers.

Exemplary fluorescent dyes that may be detected using system 6010 include a fluorescein derivative, such as carboxyfluorescein (FAM), and a PULSAR 650 dye (a derivative of Ru(bpy)3). FAM has a relatively small Stokes shift, while PULSAR 650 dye has a very large Stokes shift. Both FAM and PULSAR 650 dye may be excited with light of approximately 460-480 nm. FAM emits light with a maximum of about 520 nm (and not substantially at 650 nm), while PULSAR 650 dye emits light with a maximum of about 650 nm (and not substantially at 520 nm). Carboxyfluorescein may be paired in a probe with, for example, BLACK HOLE Quencher™1 dye, and PULSAR 650 dye may be paired in a probe with, for example, BLACK HOLE Quencher™2 dye.

More specifically, the fluorescence and/or absorbance properties of the fill control marker should be different from that of the one or more dPCR probe(s). This is of advantage in order to allow to conveniently distinguish the fill control marker and the fluorescent dPCR probe(s). However, the detection can be further simplified, if the fill control marker has an excitation wavelength or an emission wavelength identical to a target probe fluorescence marker used in the dPCR. This way the fill control does not reduce the color multiplexing capability of the detection system. As an example, the system may have 4 excitation and 4 emission channels. The large Stokes shift dye is excited by excitation wavelength 1 and the emission is collected from emission channel 4, which are also used for dPCR.

In another more particular embodiment, the fill control marker has a Stokes-shift of at least 100 nm, specifically at least 150 nm. Stokes shift is the difference (in wavelength) between positions of the band maxima of the absorption and emission spectra of the same electronic transition. When a molecule absorbs a photon, it gains energy and enters an excited state. As a result it emits a photon, thus losing its energy. When the emitted photon has less energy than the absorbed photon, this energy difference is the Stokes shift. A larger Stokes shift eliminates spectral overlap between absorption and emission and allows detection of fluorescence while reducing interference. The main advantage is that a large Stokes shift dye can be used together with other dyes having either a similar excitation or emission spectrum. Since one of both spectra, however, does not overlap between the small and the large Stokes shift dyes, spectral crosstalk is small.

Particular fill control markers include ATTO 430LS and ATTO 490LS (available from ATTO-TEC GmbH, Siegen, DE), especially ATTO 490LS. Both show good solubility in water and a Stokes-Shift of more than 100 nm, which particularly useful in methods with multiple fluorescence markers, as the high Stokes Shift minimizes an overlap of signals during detection. ATTO 490LS has the excitation wavelength of FAM and the emission wavelength of Cy5. If combined with FAM and Cy5, no additional filters for measuring ATTO 490LS are required.

In another particular embodiment of the methods of the present disclosure according to the first and second aspect the nucleic acid of interest is a nucleic acid selected from the group consisting of DNA, cDNA, RNA and a mixture thereof, or is any other type of nucleic acid.

As detailed above, the nucleic acid of interest may be any nucleic acid suitable for dPCR. The nucleic acid has to have a suitable length. It may contain non nucleic acid components. It may be naturally occurring, chemically synthesized or biotechnologically engineered. Specifically, the nucleic acid is selected from the group consisting of DNA, cDNA, RNA and a mixture thereof.

The methods of the disclosure are of particular interest in the medical field such as in diagnosis or in therapeutic monitoring and may be used in order to detect and/or quantify a nucleic acid of interest indicative of a specific microorganism, cell, virus, bacterium, fungus, mammal species, genetic status or a disease. In accordance with this, the methods may be used in the detection of a pathogen. A pathogen has the potential to cause a disease. Typically pathogen is used to describe an infectious agent such as a virus, bacterium, prion, a fungus, or even another microorganism. Of cause, the methods of the disclosure may also be used to detect non-pathogenic microorganisms.

Exemplary pathogens include without limitation:
Bacterial: *Streptococcus, Staphylococcus, Pseudomonas, Burkholderia, Mycobacterium, Chlamydophila, Ehrlichia, Rickettsia, Salmonella, Neisseria, Brucella, Mycobacterium, Nocardia, Listeria, Francisella, Legionella*, and *Yersinia*
Viral: Adenovirus, Herpes simplex, Varicella-zoster virus, Cytomegalovirus Papillomavirus, Hepatitis B virus Hepatitis C virus, Hepatitis E virus, Poliovirus, Yellow fever virus, Dengue virus, West Nile virus, TBE virus, HIV, Influenza virus, Lassa virus, Rotavirus and Ebola virus
Fungal: *Candida, Aspergillus, Cryptococcus*, Histoplasma, Pneumocystis and *Stachybotrys*
Parasites: protozoan parasites, helminth parasites and arthropod parasites In still another particular embodiment of the methods of the present disclosure according to the second aspect the sample has been obtained from a cell culture or a source suspected of being contaminated, particularly a body fluid, blood, blood plasma, blood serum, urine, bile, cerebrospinal fluid, a swab, a clinical specimen, an organ sample or a tissue sample or a subject, particularly a human, an animal or a plant, especially a human.

As detailed above, "sample" means a quantity of material that is suspected of containing a nucleic acid of interest that is to be quantified. As used herein, the term includes a specimen (e.g., a biopsy or medical specimen) or a culture (e.g., microbiological culture). Samples may be from a plant or animal, including human, it may be fluid, solid (e.g., stool) or tissue. Samples may include materials taken from a patient including, but not limited to cultures, blood, saliva, cerebral spinal fluid, pleural fluid, milk, lymph, sputum, semen, needle aspirates, and the like. The sample may be obtained from all of the various families of domestic animals, as well as feral or wild animals, including, but not limited to, such animals as ungulates, bear, fish, rodents, etc. In regard to a human sample or "tissue sample" or "patient sample" or "patient cell or tissue sample" or "specimen," each means a collection of similar cells or biological or biochemical compounds obtained from a tissue of a subject or patient. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. The tissue sample may contain compounds which are not naturally intermixed with the tissue in nature such as preservatives, anticoagulants, buffers, fixatives, nutrients, antibiotics, or the like.

In dPCR, the reaction area may be a miniaturized chamber of a microarray or a nanoarray, a chamber of a microfluidic device, a microwell or a nanowell, on a chip, in a capillary, on a nucleic acid binding surface or on a bead, especially in a microarray or on a chip.

There is a multitude of dPCR systems available, which may be used in the present disclosure. Commercialized digital PCR platforms include micro-well chip-based Bio-Mark® dPCR from Fluidigm, through hole-based QuantStudio12k flex dPCR and 3D dPCR from Life Technologies, and droplet-based ddPCR (ddPCR) QX100 and QX200 from Bio-Rad® and RainDrop from RainDance®. The microfluidic-chip-based dPCR can have up to several hundred reaction areas per panel. Droplet-based dPCR usually has approximately 20,000 partitioned droplets and can have up to 10,000,000 per reaction. The QuantStudio 12k dPCR performs digital PCR analysis on an OpenArray® plate which contains 64 reaction areas per subarray and 48 subarrays in total, equating to a total of 3072 reaction areas per array.

Droplet dPCR (ddPCR) is based on water-oil emulsion droplet technology. A sample is fractionated into a multitude of droplets (e.g. about 20,000) and PCR amplification of the template molecules occurs in each individual droplet. ddPCR technology uses reagents and workflows similar to those used for most standard TaqMan probe-based assays including droplet formation chemistry. Also, an intercalating dye, such as Evagreen, may be used. The massive sample reaction partitioning is a key aspect of the ddPCR technique. Non-spherical partitions (e.g. nanowells) actually have a larger area per sample volume than the same number of spherical partitions.

Typically, the accuracy and more importantly the precision of determination by dPCR may be improved by using a greater number of reaction areas. One may use approximately, 100 to 200, 200 to 300, 300 to 400, 700 or more reaction areas, which are used for determining the amount or concentration in question by PCR. In a particular embodiment of the methods of the present disclosure according to the first and second aspect the dPCR is carried out identically in at least 100 reaction areas, particularly at least 1,000 reaction areas, especially at least 5,000 reaction areas. In a particular embodiment of the methods of the present disclosure according to the first and second aspect the dPCR is carried out identically in at least 10,000 reaction areas, particularly at least 50,000 reaction areas, especially at least 100,000 reaction areas.

For example, the dPCR is carried out identically in an array having between at least 100-100,000 reaction areas, e.g., between at least 1,000-100,000 reaction sites, or between at least 10,000-100,000 reaction sites.

Specifically, the dPCR involves the use of one or more fluorescent dPCR probes in order to detect one or more nucleic acid(s) of interest, particularly in combination with a quencher or as molecular beacon or as a hydrolysis probe.

In PCR applications (such as Real Time PCR) fluorescence is often used to detect amplification products. It is usually carried out in a thermal cycler with the capacity to illuminate each sample with a beam of light of at least one specified wavelength and detect the fluorescence emitted by the excited fluorophore. The thermal cycler is also able to rapidly heat and chill samples, thereby taking advantage of the physicochemical properties of the nucleic acids and DNA polymerase.

The dPCR may involve the use of one or more fluorescent probes in order to detect the nucleic acid of interest and/or the reference nucleic acid, particularly in combination with a quencher or as molecular beacon or as a hydrolysis probe.

Often Fluorescence Resonance Energy Transfer (FRET) is detected in qPCR. FRET is a technique for measuring interactions between two molecules, in the present case two probes. In this technique, two different fluorescent molecules (fluorophores or labels) are genetically fused to a pair of probes suitable for the detection of a nucleic acid. The principle of FRET is based on the combined characteristics of the two labels. If a label is excited with a light of a particular wavelength (absorption frequency) its re-emits that energy at a different wavelength (the emission frequency). In FRET the first label is excited which in turn emits light having the emission frequency. If the emission peak of the first label (donor) overlaps with the excitation peak of the second label (acceptor), proximity of the two labels can be determined, since the first label transfers energy to the second label and the second label emits light at its own emission frequency. The net result is that the donor emits less energy than it normally would (since some of the energy it would radiate as light gets transferred to the acceptor instead), while the acceptor emits more light energy at its excitation frequency (because it is getting extra energy input from the donor fluorophore). Also the combination of a fluorescent dye with a quencher may be used. If the quencher is in proximity to the fluorescent dye, the emission of fluorescence is omitted. If the fluorescent moiety becomes separated from the quencher, the emission of the first fluorescent moiety can be detected after excitation with light of a suitable wavelength. Molecular beacons are hairpin shaped probes with an internally quenched fluorophore whose fluorescence is restored when they bind to a target nucleic acid sequence. If the nucleic acid to be detected is complementary to the strand in the loop, the duplex formed between the nucleic acid and the loop is more stable than that of the stem because the former duplex involves more base pairs. This causes the separation of the fluorophore and the quencher. Once the fluorophore is distanced from the quencher, illumination of the hybrid with light results in the fluorescent emission. The presence of the emission reports that the event of hybridization has occurred and hence the target nucleic acid sequence is present in the test sample. Hydrolysis probes consist of a fluorophore covalently attached to the 5'-end of the oligonucleotide probe and a quencher at the 3'-end. As long as the fluorophore and the quencher are in proximity, quenching inhibits any fluorescence signals. The probes are designed such that they anneal within a DNA region amplified by a specific set of primers. As the polymerase extends the primer and synthesizes the nascent strand, the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore. Hence, fluorescence detected is indicative of the presence of the nucleic acid in question.

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatephenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC-Red 610, LC-Red 640, LC-Red 670, LC-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

Specifically, the fluorescent probe comprises fluorescein, rhodamine and/or cyanine. For example, the donor fluorescent moiety may be fluorescein and/or the acceptor fluorescent moiety may be selected from the group consisting of LC-Red 610, LC-Red 640, LC-Red 670, LC-Red 705, Cy5, and Cy5.5, specifically LC-Red 610 or LC-Red 640. More specifically the donor fluorescent moiety is fluorescein and the acceptor fluorescent moiety is LC-Red 640 or LC-Red 610. Several different fluorophores (e.g. 6-carboxyfluorescein, acronym: FAM, or tetrachlorofluorescein, acronym: TET) and quenchers (e.g. tetramethylrhodamine, acronym: TAMRA) are available.

The definitions, and examples made in the context of the methods of the first aspect of the disclosure also apply to those of the second aspect and vice versa.

Unless defined otherwise, all technical and scientific terms and any acronyms used herein have the same meanings as commonly understood by one of ordinary skill in the art in the field of the disclosure. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The disclosure is not limited to the particular methodology, protocols, and reagents described herein because they may vary. Although any methods and materials similar or equivalent to those described herein can be used in the practice of the present disclosure, the particular methods, and materials are described herein. Further, the terminology used herein is for the purpose of describing particular embodiments only and is not intended to limit the scope of the present disclosure.

As used herein and in the appended claims, the singular forms "a," "an," and "the" include plural reference unless the context clearly dictates otherwise. Similarly, the words "comprise," "contain" and "encompass" are to be interpreted inclusively rather than exclusively. Similarly, the word "or" is intended to include "and" unless the context clearly indicates otherwise. The term "plurality" refers to two or more.

The Examples and Figures are intended to illustrate various embodiments of the disclosure. As such, the specific modifications discussed are not to be construed as limitations on the scope of the disclosure. It will be apparent to the person skilled in the art that various equivalents, changes, and modifications may be made without departing from the scope of the disclosure, and it is thus to be understood that such equivalent embodiments are to be included herein.

EXAMPLE

Example 1: Typical Steps for Carrying Out a dPCR Measurement According to the Disclosure A well-defined volume of the purified sample containing the nucleic acids is mixed with a well-defined volume of the mastermix components as used in any qPCR experiments.

In the case of microarray-based dPCR, some minor modifications of the composition may be needed, compared to a standard qPCR mastermix. These may include other detergents or different concentrations of detergents to adjust wetting properties in the microarray. Other surface-active substances may need to be added, e.g. in order to avoid adsorption of nucleic acids, polymerase or other components onto the surfaces of the chip. In some cases a dilution of the sample with the mastermix backbone may be needed. The backbone contains the same buffer components as the mastermix, but no polymerase, no nucleotides and no primers/probes. The reaction mix containing sample and mastermix is then manually pipetted into the inlet port of a dPCR microarray plate.

A dPCR plate may hold 1-8 reaction mixes (samples) within the format of a standard microwell plate (SBS format). Each of the 1-8 sample positions within the dPCR plate may consist of an inlet port, e.g. at position A1 of the plate, the microstructured part between positions A1 and A12, and an outlet port at position A12. As a next process step a partitioning fluid is added to each of the inlet. This can be done manually, using a single or a 8-channel pipette, or by using an automated dispense station. The separation or partitioning fluid is a hydrophobic liquid which is immiscible and unreactive with respect to the reaction mix, e.g. a long-chain fluorinated hydrocarbon or a silicon oil. The separation of the individual reaction areas containing reaction mix (or partitioning) can be done passively, or by applying overpressure at the inlet ports, or by applying underpressure at the outlet ports. Passive separation may work, if a low-viscosity separation fluid is used, or if the process is done at elevated temperature. At higher viscosities, an overpressure of typically 100-1000 mbar must be applied to complete the separation process within about 1 minute. If the separation process is done with an automated device, and if separation speed may vary from sample to sample, monitoring sensors must make sure that the process stops when the separation is complete, i.e. the separation fluid has reached the outlet port. Thereafter the dPCR plate is transferred to the thermal cycler unit. The transfer may occur plate by plate, or by transferring a stack of plates at once. The transfer process can be fully automated, or the transfer of the stack of plates can be manual, while the rest of the dPCR process, including thermal cycling and readout, is fully automated. The thermal cycling process is similar to any end-point thermal cycling process, with typically 30-60 thermal cycles, each cycle consisting of a denaturation step at 92-96° C. for 10-30 s, and an annealing/extension step at 55-60° C. for 40-60 s. A pre-PCR cycle at 92-96° C. for 30-300 s and a cool down cycle or ramp down to 30-40° C. may also be needed. It may be necessary to carry out thermal cycling at an elevated pressure, in order to suppress the generation and expansion of bubbles (of air and water vapor) within the microarray. In this case the pressure must be built up before the first heat up of the dPCR plate, and be released after the dPCR plate has been cooled down. If a high throughput of dPCR results is required, it may be necessary to have a number of thermal cycler units working essentially in parallel.

After completion of the thermal cycling process, dPCR plates are sequentially transferred to the reader unit, and after readout to an output stack position within the automated dPCR analyzer. As the fluorescence reader may require a sufficient resolution to distinguish fluorescence signal from neighboring reaction areas, and as the microstructured area belonging to a sample is large (typically 6 mm×90 mm), several fluorescence images may be needed per sample. For this purpose either the fluorescence imager or the dPCR plate must be moved to the different image positions. In order to keep the overall reading time low, a particular reader embodiment would have a large field of view, ideally allowing to image two sample lanes in the same position. In each imaging position, an autofocus adjustment may be needed. This may be done in a fluorescence mode, in a brightfield or a darkfield mode. It may also be necessary to correct for tilts between the camera plane and the image plane containing the reaction areas. Furthermore, various combinations of excitation and emission filter positions may be needed for acquisition of the different fluorescent markers, including the fill control marker.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A method for reducing quantification errors caused by reaction volume deviations in digital polymerase chain reaction (dPCR), wherein the amount or concentration of a nucleic acid of interest is quantified in an array of reaction areas, the method comprising
   a) adding a fill control marker to each reaction area of the array of reaction areas used in dPCR;
   b) quantifying the reaction volume in each reaction area; and
   c) calculating the amount or concentration of the nucleic acid of interest as a number of nucleic acid(s) as determined by dPCR in a volume or per volume, wherein the volume is the sum of the reaction volumes as determined in step b).

2. A method for determining the amount or concentration of a nucleic acid of interest in a sample, the method comprising the steps of:
   a) providing a sample suspected of containing the nucleic acid of interest;
   b) performing a dPCR with the sample in each reaction area of an array of reaction areas;

c) quantifying the reaction volume in each reaction area; and d) calculating the amount or concentration of the nucleic acid of interest as a number of nucleic acid(s) as determined in step b) in a volume or per volume, wherein the volume is the sum of the reaction volumes as determined in step c).

3. The method of claim 1, wherein the reaction volume is quantified by quantifying a fill control marker present in each reaction area.

4. The method of claim 3, wherein the signal of the fill control marker is proportional to the reaction volume in the reaction area.

5. The method of claim 3, wherein a correction factor for each reaction area is calculated based on the signal of the fill control marker measured and the signal of the fill control marker expected and wherein the correction factor accounting for a reaction volume deviation is applied to the respective reaction area.

6. The method of claim 1, wherein the reaction volume in each reaction area is quantified based on the height of the reaction volume in the reaction area.

7. The method of claim 1, wherein a reaction area is identified as invalid, if the quantity of the fill control marker in the reaction area does not match a threshold.

8. The method of claim 7, wherein the reaction area is identified as invalid if the quantity of the fill control marker in the reaction area is below a lower threshold.

9. The method of claim 7, wherein the reaction area is identified as invalid if the quantity of the fill control marker in the reaction area is above an upper threshold.

10. The method of claim 1, wherein the fill control marker is added to the PCR reaction mix before being distributed to the reaction areas.

11. The method of claim 1, wherein the fill control marker is a fluorescence marker or an absorbance marker.

12. The method of claim 8, wherein the fill control marker has one or more of the following characteristics:

has fluorescence and/or absorbance properties different from that of one or more dPCR probe(s);

has an excitation wavelength or an emission wavelength identical to a target probe fluorescence marker used in the dPCR; or has a Stokes-shift of at least 100 nm.

13. The method of claim 1, wherein the nucleic acid of interest has one or more of the following characteristics:

is a nucleic acid selected from the group consisting of DNA, cDNA, RNA and a mixture thereof; or is indicative of a microorganism, a cell, a virus, a bacterium, a fungus, a mammal species, a genetic status or a disease.

14. The method of claim 2, wherein the sample has been obtained from a cell culture or a source suspected of being contaminated.

15. The method of claim 14, wherein the sample comprises a body fluid, blood, blood plasma, blood serum, urine, bile, cerebrospinal fluid, a swab, a clinical specimen, an organ sample or a tissue sample.

16. The method of claim 1, wherein the reaction area is selected from the group consisting of a miniaturized chamber of a microarray; a miniaturized chamber of a nanoarray; a chamber of a microfluidic device; a microwell on a chip; a nanowell on a chip; a microwell in a capillary; a nanowell in a capillary; a nucleic acid binding surface; and a bead.

17. The method of claim 1, wherein the array of reaction areas comprises at least 100 reaction areas.

18. The method of claim 1, wherein the array of reaction areas comprises at least 100-100,000 reaction areas.

19. The method of claim 1, wherein the array of reaction areas comprises at least 10,000-100,000 reaction areas.

20. The method of claim 1, wherein the dPCR involves the use of one or more fluorescent dPCR probes in order to detect one or more nucleic acid(s) of interest, alone or in combination with a quencher.

* * * * *